United States Patent
Vincent et al.

(10) Patent No.: US 10,307,733 B2
(45) Date of Patent: Jun. 4, 2019

(54) GUARD BED MATERIAL, ITS METHOD OF MAKING AND USE

(71) Applicant: ExxonMobil Chemical Patents Inc., Baytown, TX (US)

(72) Inventors: Matthew J. Vincent, Kingwood, TX (US); Terry E. Helton, Montgomery, TX (US); Jenna L. Walp, Bethlehem, PA (US); Dominick A. Zurlo, IV, Easton, PA (US); Doug F. Colmyer, Spinnerstown, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 145 days.

(21) Appl. No.: 15/523,250

(22) PCT Filed: Nov. 11, 2015

(86) PCT No.: PCT/US2015/060129
§ 371 (c)(1),
(2) Date: Apr. 28, 2017

(87) PCT Pub. No.: WO2016/099715
PCT Pub. Date: Jun. 23, 2016

(65) Prior Publication Data
US 2017/0333873 A1      Nov. 23, 2017

Related U.S. Application Data

(60) Provisional application No. 62/093,850, filed on Dec. 18, 2014.

(30) Foreign Application Priority Data

Mar. 9, 2015   (EP) ................................. 15158209

(51) Int. Cl.
| | | |
|---|---|---|
| B01J 38/56 | (2006.01) | |
| B01J 20/34 | (2006.01) | |
| C07C 2/66 | (2006.01) | |
| C07C 6/12 | (2006.01) | |
| B01D 15/00 | (2006.01) | |
| B01J 29/04 | (2006.01) | |
| C07C 7/04 | (2006.01) | |
| C07C 7/11 | (2006.01) | |
| C07C 15/04 | (2006.01) | |
| C07C 15/073 | (2006.01) | |
| C07C 15/085 | (2006.01) | |

(52) U.S. Cl.
CPC .......... *B01J 20/3408* (2013.01); *B01D 15/00* (2013.01); *B01J 29/04* (2013.01); *C07C 2/66* (2013.01); *C07C 6/126* (2013.01); *C07C 7/04* (2013.01); *C07C 7/11* (2013.01); *C07C 15/04* (2013.01); *C07C 15/073* (2013.01); *C07C 15/085* (2013.01); *C07C 2529/06* (2013.01); *C07C 2529/08* (2013.01); *C07C 2529/18* (2013.01); *Y02P 20/52* (2015.11)

(58) Field of Classification Search
CPC ..... B01J 20/3408; B01J 29/04; C07C 15/073; C07C 15/04; C07C 7/11; C07C 7/04; C07C 15/085; C07C 6/126; C07C 2/66; C07C 2529/08; C07C 2529/06; C07C 2529/18; B01D 15/00; Y02P 20/52
See application file for complete search history.

(56) References Cited

U.S. PATENT DOCUMENTS

| | | |
|---|---|---|
| 8,877,996 B2 | 11/2014 | Vincent et al. |
| 2009/0036722 A1 | 2/2009 | Clark et al. |
| 2010/0076237 A1 | 3/2010 | Clark et al. |
| 2012/0157739 A1 | 6/2012 | Jan et al. |
| 2013/0211164 A1* | 8/2013 | Vincent ................. C07C 2/66 585/323 |

FOREIGN PATENT DOCUMENTS

| | | | |
|---|---|---|---|
| CN | 103418421 | 12/2013 | |
| WO | 93/00992 | 1/1993 | |
| WO | 2008/016636 | 2/2008 | |
| WO | WO-2008098676 A1 * | 8/2008 | ............... C07C 2/66 |

* cited by examiner

*Primary Examiner* — Haytham Soliman
(74) *Attorney, Agent, or Firm* — Darryl M. Tyus

(57) ABSTRACT

The present disclosure relates to a material preferably used in a guard bed, and having an increased capacity to adsorb catalyst poisons, as measured by collidine update at 200° C. The material is made by a method in which it is treated by being dried with a drying gas, preferably, at a temperature greater than about 200° C. The treated material may be used to remove impurities from untreated feed streams to, for example, aromatic alkylation and transalkylation processes, where such impurities act as catalyst poisons that cause deactivation of the acidic molecular sieve-based catalysts used, thereby increasing the cycle length of such catalysts.

17 Claims, No Drawings

GUARD BED MATERIAL, ITS METHOD OF MAKING AND USE

CROSS REFERENCE TO RELATED APPLICATIONS

This application is a U.S. National Stage Application of International Application Serial No. PCT/US2015/060129 filed Nov. 11, 2015 and claims priority to and the benefit of U.S. Provisional Application Ser. No. 62/093,850, filed Dec. 18, 2014, which are incorporated herein by reference in their entireties.

FIELD OF THE INVENTION

The present invention relates to a material, preferably a guard bed material, having an increased capacity to adsorb catalyst poisons, as measured by collidine uptake at 200° C., and to methods of making such material. The present invention also relates to the use of the material in a method for removing catalyst poisons from untreated feed streams having one or more impurities which cause deactivation of the downstream catalysts employed in processes, such as those that produce mono-alkylated aromatic compounds. As a result, the cycle length of such catalysts is increased.

BACKGROUND OF THE INVENTION

In a typical aromatic alkylation process, an aromatic compound is reacted with an alkylating agent, such as an olefin, in the presence of acid catalyst. For example, benzene can be reacted with ethylene or propylene to produce ethylbenzene or cumene, both of which are important intermediates in the chemical industry. In the past, commercial aromatic alkylation processes normally used $AlCl_3$ or $BF_3$ as the acid catalyst, but more recently these materials have been replaced by molecular sieve-based catalysts.

Aromatics alkylation processes employing molecular sieve-based catalysts may be conducted in either the vapor phase or the liquid phase. However, in view of the improved selectivity and decreased capital and operating costs associated with liquid phase operation, most commercial alkylation processes now operate under at least partial liquid phase conditions. Unfortunately, one disadvantage of operating under liquid phase conditions is that the molecular sieve-based catalysts tend to be more sensitive to the presence of catalyst poisons in the feed streams, especially those with a compound having at least one of the following elements: nitrogen, halogens, oxygen, sulfur, arsenic, selenium, tellurium, phosphorus, and Group 1 through Group 12 metals. Such impurities reduce the acid activity of such molecular sieve-based catalyst and hence decrease the cycle time between required regenerations of such catalyst.

The use of guard beds to remove trace contaminants from hydrocarbon feed streams is well known in the art. This is especially true for petrochemical and specialty chemical operations where product purity is critical. Normally, guard bed materials that contain bentonite clay, kaolin clay, special activated aluminas or molecular sieves are used and are placed upstream of a reaction vessel containing an acidic molecular sieve-based catalyst. These guard bed materials trap impurities in the feed streams so that product purity specifications can be met and poisoning of such catalyst can be reduced. However, such guard bed materials have limited capacity to adsorb impurities from aromatic feed streams to the low levels required for use in liquid phase alkylation processes which employ acidic molecular sieve-based catalysts. Therefore, a need exists for a guard bed material with an increased capacity to adsorb impurities more effectively. It is desirable to remove such impurities from the feed streams to such aromatic alkylation processes and thereby reduce the deactivation of the downstream acidic molecular sieve-based catalyst used in alkylation and/or transalkylation reactions.

According to the present invention, it has now been found that the capacity to adsorb catalyst poisons of a guard bed material, as measured by collidine update at 200° C., may be increased by a method in which an untreated guard bed material is dried with a drying gas at a temperature of greater than 200° C. to produce the treated guard bed material. Optionally, the guard bed catalyst may be contacted with water or humid gas prior to being dried. The treated guard bed material may be used to remove impurities from untreated feed streams to aromatic alkylation processes, thereby increasing the cycle length of such catalysts.

SUMMARY OF THE INVENTION

In one aspect, the invention relates to a material, preferably a guard bed material, having an increased capacity to adsorb catalyst poisons. The material preferably comprising a molecular sieve, and having an increased collidine uptake at 200° C. after drying with a drying gas, preferably, at a temperature of greater than about 200° C., and in some embodiments, up to a temperature less than or equal to about 550° C. In one or more embodiments, the guard bed material may be optionally contacted with water or a humid gas before being dried. In one or more embodiments, the humid gas is selected from the group consisting of air, oxygen, nitrogen and mixtures thereof.

In one or more embodiments, the molecular sieve of the guard bed material may be a large pore zeolite having a Constraint Index of less than 2. Such large pore zeolites include, but are not limited to, a molecular sieve having a framework structure type selected from the group consisting of FAU, *BEA, MWW, MOR and mixtures thereof.

In another aspect, the invention relates to a method for making the material, described above, the method comprising the step of drying an untreated guard bed material having a first collidine uptake at 200° C. with a drying gas, preferably, at a temperature greater than about 200° C., and in some embodiments, up to a temperature less than or equal to about 550° C., to produce said guard bed material having said an increased collidine uptake at 200° C., for example, a second collidine uptake that is greater than the first collidine uptake at 200° C. of said untreated guard bed material that is not contacted with water or humid gas and/or dried. The material preferably comprises a molecular sieve. The method may be practiced inside of a vessel (i.e., in-situ), for example in a guard bed vessel, or outside of a vessel (i.e., ex-situ). The invention includes a guard bed material made by the method above.

In another aspect, the invention relates to a method for removing catalyst poisons from an untreated feed stream having one or more impurities, the method comprising the step of contacting an untreated stream with the material of this invention or the material made by one of the methods of this invention, to remove at least a portion of said impurities and to produce a treated feed stream having a reduced amount of impurities, wherein said untreated stream comprising one or more alkylatable aromatic compound streams, optionally one or more alkylating agent streams, wherein said impurities comprising compounds having at least one of the following elements: nitrogen, halogens, oxygen, sulfur, arsenic, selenium, tellurium, phosphorus, and Group 1 through Group 12 metals.

In still another aspect, the invention relates to a process for producing a mono-alkylated aromatic compound stream comprising the step of contacting a treated feed stream and an alkylating agent stream with an alkylation or transalkylation catalyst composition under alkylation or transalkylation conditions to produce an effluent stream comprising said mono-alkylated aromatic compound stream. In one or more embodiments, the treated feed stream is made by the method for removing catalyst poisons of this invention, described above.

In still yet another aspect, the invention relates to a process for producing a mono-alkylated aromatic compound stream comprising the steps of:

(a) contacting a material with a humid gas, and then drying said material with a drying gas at a temperature greater than about 200° C. to produce a guard bed material having an increased collidine uptake at 200° C., wherein said humid gas has a relative humidity in the range of greater than or equal to about 50% to less than or equal to about 100%;

(b) contacting an untreated stream having one or more impurities with said guard bed material of step (a) to remove at least a portion of said impurities and to produce a treated feed stream having a reduced amount of impurities, wherein said untreated stream comprising one or more alkylatable aromatic compound streams, optionally one or more alkylating agent streams; and (c) contacting said treated feed stream of step (b) and an alkylating agent stream with an alkylation or transalkylation catalyst composition under alkylation or transalkylation conditions to produce an effluent stream comprising said mono-alkylated aromatic compound stream.

In one or more embodiments, the process further comprising a guard bed vessel which contains said material, wherein said drying of the material is conducted in-situ in said guard bed vessel.

DETAILED DESCRIPTION OF THE INVENTION

Definitions

The terms "a" and "the" as used herein are understood to encompass the plural as well as the singular.

The term "alkylatable aromatic compound" as used herein means an aromatic compound that may receive an alkyl group. One non-limiting example of an alkylatable aromatic compound is benzene.

The term "alkylating agent" as used herein means a compound which may donate an alkyl group to an alkylatable aromatic compound. Non-limiting examples of an alkylating agent are ethylene, propylene, and butylene. Another non-limiting example is any poly-alkylated aromatic compound that is capable of donating an alkyl group to an alkylatable aromatic compound.

The term "aromatic" as used herein in reference to the alkylatable aromatic compounds which are useful herein is to be understood in accordance with its art-recognized scope which includes substituted and unsubstituted mono- and polynuclear compounds. Compounds of an aromatic character which possess a heteroatom (e.g., N or S) are also useful provided they do not act as impurities, as defined below, under the reaction conditions selected.

The term "catalyst deposit height" as used herein means the smallest thickness, when deposited, among all dimensions of the deposited guard bed material.

The term "catalyst poison" as used herein means one or more impurities, as defined herein, which acts to reduce the cycle length of a molecular sieve or a catalyst.

The term "collidine uptake at 200° C." as used herein means amount of collidine adsorbed by a material as determined in accordance with the collidine adsorption test, as set forth hereinafter.

The term "comprising" (and its grammatical variations) as used herein is used in the inclusive sense of "having" or "including" and not in the exclusive sense of "consisting only of."

The term "Constraint Index" as used herein is a convenient measure of the extent to which an aluminosilicate or molecular sieve provides controlled access to molecules of varying sizes to its internal structure. For example, aluminosilicates or molecular sieves which provide a highly restricted access to and egress from its internal structure have a high value for the Constraint Index, and aluminosilicates or molecular sieves of this kind usually have pores of small size, e.g. less than 5 Angstroms. On the other hand, aluminosilicates or molecular sieves which provide relatively free access to the internal aluminosilicate structure have a low value for the constraint index, and usually pores of large size. The method by which Constraint Index may be determined is described fully in U.S. Pat. No. 4,016,218, incorporated herein by reference.

The term "cycle length" as used herein means the total on-oil time between regenerations, or the on-oil time period between fresh load and regeneration. After the fresh catalyst or the regenerated catalyst being brought on-oil, the catalyst may be deactivated due to coke deposition or adsorption of catalyst poisons. As the catalyst becomes deactivated, the reaction zone has to be operated at higher temperatures to maintain the same productivity or catalytic activity. The catalyst has to be regenerated once the reaction zone temperature reaches a threshold temperature, typically determined by metallurgy of the reactor or when economic factors warrant.

The term "at least partially liquid phase" as used herein, means a mixture having at least 1 wt. % liquid phase, optionally at least 5 wt. % liquid phase, at a given temperature, pressure, and composition.

The term "at least partially deactivated", or "deactivated", when used in connection with the guard bed material, the alkylation catalyst, or the transalkylation catalyst herein means that the catalytic activity of such material or catalyst has decreased by an amount of at least 1% as compared to initial catalytic activity of the fresh guard bed material, or the fresh alkylation catalyst or the fresh transalkylation catalyst.

The term "framework type" as used herein has the meaning described in the "Atlas of Zeolite Framework Types," by Ch. Baerlocher, W. M. Meier and D. H. Olson (Elsevier, 5th Ed., 2001).

The term "fresh" when used in connection with the molecular sieve, the guard bed material, the alkylation catalyst, or the transalkylation catalyst herein means the molecular sieve or such catalyst has not been used in a catalytic reaction after being manufactured.

The term "impurities" as used herein includes, but is not limited to, compounds having at least one of the following elements: nitrogen, halogens, oxygen, sulfur, arsenic, selenium, tellurium, phosphorus, and Group 1 through Group 12 metals. Such impurities, includes, but is not in any way limited to, organic nitrogenous impurities.

The term "MCM-22 family material" (or "MCM-22 family molecular sieve"), as used herein, can include:

(i) molecular sieves made from a common first degree crystalline building block "unit cell having the MWW framework topology." A unit cell is a spatial arrangement of atoms which is tiled in three-dimensional space to describe the crystal as described in the "Atlas of Zeolite Framework Types," by Ch. Baerlocher, W. M. Meier and D. H. Olson (Elsevier, 5th Ed., 2001);

(ii) molecular sieves made from a common second degree building block, a 2-dimensional tiling of such MWW framework type unit cells, forming a "monolayer of one unit cell thickness," preferably one c-unit cell thickness;

(iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, and any combination thereof; or (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system.

Members of the MCM-22 family include, but are not limited to, MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and UZM-8HS (described in U.S. Pat. No. 7,713,513); and an EMM-10 family molecular sieve (described or characterized in U.S. Pat. Nos. 7,959,899 and 8,110,176; and U.S. Patent Application Publication No. 2008/0045768), such as EMM-10, EMM-10-P, EMM-12 and EMM-13.

The term "mono-alkylated aromatic compound" means an aromatic compound that has only one alkyl substituent. Non-limiting examples of mono-alkylated aromatic compounds are ethylbenzene, isopropylbenzene (cumene) and sec-butylbenzene.

The term "poly-alkylated aromatic compound" as used herein means an aromatic compound that has more than one alkyl substituent. A non-limiting example of a poly-alkylated aromatic compound is poly-alkylated benzene, e.g., di-ethylbenzene, tri-ethylbenzene, di-isopropylbenzene, and tri-isopropylbenzene.

The term "regenerated" when used in connection with the guard bed material, the alkylation catalyst, or the transalkylation catalyst herein means an at least partially deactivated guard bed material or catalyst that has been treated under controlled conditions of oxygen content and temperature to remove at least a portion of the coke deposited or to remove at least a portion of adsorbed catalyst poisons and thereby increase the catalytic activity of such material or catalyst.

Guard Bed Material

The material of this invention, preferably a guard bed material, has an increased capacity to adsorb catalyst poisons as measured by collidine uptake at 200° C., after being made by one or more methods of this invention.

The guard bed material comprises a molecular sieve, and in one or more embodiments, the molecular sieve that may be used in this invention is a large pore zeolite having a Constraint Index of less than 2. Such large pore zeolites include, but are not limited to, for example, a molecular sieve having a framework structure type selected from the group consisting of FAU, *BEA, MWW, MOR and mixtures thereof. Other suitable large pore zeolites that may be used in this invention include, but are not limited to, ZSM-3, ZSM-4, ZSM-14, ZSM-18, and ZSM-20, as well as Linde Type X, Linde type A and mixtures thereof.

The molecular sieve having a FAU framework structure type is selected from the group consisting of zeolite Y, low sodium ultrastable Y (USY), dealuminized Y (Deal Y), ultrahydrophobic Y (UHP-Y), rare earth exchanged Y (REY), rare earth exchanged USY (RE-USY), zeolite X, and mixtures thereof. The molecular sieve having a *BEA framework structure type is zeolite beta. The molecular sieve having a MWW framework structure type is a MCM-22 family material, as defined herein. The MCM-22 family material of this invention includes one or more of ERB-1, ITQ-1, ITQ-2, ITQ-30, PSH-3, SSZ-25, MCM-22, MCM-36, MCM-49, MCM-56, UZM-8, EMM-10, EMM-10P, EMM-12, EMM-13 and mixtures thereof. The molecular sieve having a MOR framework structure type is selected from the group consisting of mordenite, TEA-mordenite and mixtures thereof.

Zeolite ZSM-3 is described in U.S. Pat. No. 3,415,736. Zeolite ZSM-18 is described in U.S. Pat. No. 3,950,496. Linde Type X is described in French Patent No. 1,117,756. Linde Type A is described in French Patent No. 1,117,776. Zeolite ZSM-14 is described in U.S. Pat. No. 3,923,636. Zeolite ZSM-20 is described in U.S. Pat. No. 3,972,983. Zeolite beta is described in U.S. Pat. No. 3,308,069, and U.S. Reissue Pat. 28,341. Low sodium ultrastable Y molecular sieve (USY) and rare earth exchanged USY (RE-USY) are described in U.S. Pat. Nos. 3,293,192 and 3,449,070. Dealuminized Y zeolite (Deal Y) may be prepared by the method found in U.S. Pat. No. 3,442,795.

Ultrahydrophobic Y (UHP-Y) is described in U.S. Pat. No. 4,401,556. Rare earth exchanged Y (REY) is described in U.S. Pat. No. 3,524,820. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

In one or more embodiments, the guard bed material comprises a fresh molecular sieve, an at least partially deactivated molecular sieve, or combinations thereof. In one or more embodiments, the at least partially deactivated guard bed material, for example, may have been deactivated by coke deposition during prior use in an alkylation or transalkylation process, or deactivated during prior use as an adsorbent of impurities.

Method of Making the Material

The method of making the material, preferably a guard bed material, of this invention comprising the step of drying an untreated guard bed material having a first collidine uptake at 200° C. with a drying gas, preferably, drying at a temperature greater than about 200° C., and in some embodiments, up to a temperature less than or equal to about 550° C., to produce said guard bed material having said an increased collidine uptake at 200° C., for example, a second collidine uptake that is greater than the first collidine uptake at 200° C. of said untreated guard bed material that is not contacted with water or humid gas and/or dried.

In one or more embodiments, drying the material with a drying gas at a temperature in a range from about 200° C., or 250° C., or 300° C., or 350° C. or 400° C., or 450° C., or 500° C. up to less than or equal to about 550° C. In one or more embodiments, the guard bed material is dried at a temperature in the range of from greater than or equal to about 200° C. to less than or equal to about 550° C., or in the range from greater than or equal to about 250° C. to less than or equal to about 550° C., or in the range from greater than or equal to about 300° C. to less than or equal to about 500° C. In other embodiments, the guard bed material is dried at a temperature in the range of from less than 600° C., or less than 550° C., or less than 500° C., or less than 450° C. up to greater than 200° C., or greater than 250° C., or greater than 300° C.

The drying gas can be any gas that is not reactive under the drying conditions, such as air, nitrogen, oxygen, or any other suitable gas, including mixtures thereof. In one or more embodiments, the drying gas may be selected from the group consisting of air, oxygen, nitrogen and mixtures thereof.

The drying of the material can be conducted with flowing drying gas. The drying gas can flow at any direction. In one embodiment, the drying gas can flow along the direction of the material deposit height through the material (perpendicular), or can flow along the direction (vertical) to the material deposit height.

The dryer can be a fixed or moving shallow dryer. Non-limiting examples of such dryers include a shallow moving bed dryer or a shallow moving bed tray. The term "shallow" as used herein means that the depth of the dryer is less than about 1 meter, or less than about 50 centimeters, or less than about 20 centimeters, or less than about 25 centimeters, or less than about 10 centimeters, for example, about 8 centimeters or less, about 5 centimeters or less, or about 3 centimeters or less.

In some embodiments, the guard bed material during the drying can be deposited in a dryer at a material deposit height of less than about 1 meter. In other embodiments, less than about 50 centimeters, or less than about 25 centimeters, or less than about 20 centimeters, or less than about 10 centimeters; for example, about 9 centimeters or less, about 8 centimeters or less, about 7 centimeters or less, about 6 centimeters or less, about 5 centimeters or less, about 4 centimeters or less, or about 3 centimeters or less, about 2 centimeters or less; about 1 centimeter or less. In some embodiments, the material can be deposited in a material deposit height of about 0.1 centimeter or more, for example, about 0.2 centimeter or more, about 0.1 centimeter or more, about 0.2 centimeter or more, about 0.3 centimeter or more, about 0.4 centimeter or more, about 0.5 centimeter or more, about 0.6 centimeter or more, about 0.7 centimeter or more, about 0.8 centimeter or more, about 0.9 centimeter or more. In some embodiments, the material can be deposited in a material deposit height ranging from any two values as above described so long as the low limit value is less than the upper limit value; for example, from about 0.1 to about 10 centimeters, or from about 0.5 to about 8 centimeters, or from about 1 to about 5 centimeters.

The drying can be conducted for a period of greater than about 1 minute; for example, from 1 minute to about 96 hours in one embodiment, or about 30 minutes to 48 hours in another embodiment, or about 1 hour to 36 hours in still another embodiment, or about 2 hours to about 24 hours in yet another embodiment.

In one or more embodiments, the method of making the material of this invention may include the step of contacting the material with water and/or with humid gas before being dried, and thereafter having an increased collidine uptake at 200° C., for example, a collidine uptake at 200° C. that is greater than said collidine uptake at 200° C. of an untreated guard bed material that is not dried and/or contacted with water or humid gas and/or dried.

In one or more embodiments, the guard bed material comprising a molecular sieve is contacted with water or humid gas to form a humidified guard bed material having a Loss-On-Ignition (LOI), as defined herein, that is greater than a guard bed material that is not contacted with water or humid gas. The humidified guard bed material is thereafter dried with a drying gas, preferably, at a temperature greater than or equal to 200° C. to form the guard bed material of this invention having an increased collidine uptake at 200° C., for example, a collidine uptake at 200° C. that is greater than said collidine uptake at 200° C. of an untreated guard bed material not contacted with water or humid gas and dried.

The water may be liquid water and have a temperature in the range of greater than or equal to about 0° C., or 25° C., or 50° C., or 75° C. up to less than or equal to about 100° C. In one or more embodiments, the water may have a temperature in the range of greater than or equal to about 0° C. to less than or equal to about 100° C., or in the range of greater than or equal to 25° C. to less than or equal to 100° C., or in the range of greater than or equal to 25° C. to less than or equal to 75° C., or in the range of greater than or equal to 0° C. to less than or equal to 50° C.

The humid gas may have a relative humidity in the range of greater than or equal to about 10%, or 15%, or 20%, or 30%, or 50%, or 60%, or 70%, or 80%, or 90% up to less than or equal to about 100%. In one or more embodiments, the humid gas may have a relative humidity in the range of greater than or equal to about 50% to less than or equal to about 100%, or in the range of greater than or equal to 50% to less than or equal to 75%, or in the range of at least 1% to less than or equal to 100%.

The humid gas may be comprised of air, or oxygen, or nitrogen or other gaseous fluid. In one or more embodiments, the humid gas may be selected from the group consisting of air, oxygen, nitrogen and mixtures thereof.

Method for Removing Catalyst Poisons

The method for removing catalyst poisons from an untreated feed stream having one or more impurities, comprising the step of contacting an untreated stream with the material of this invention or the material made by one of the methods of this invention. At least a portion of said impurities are removed from the untreated stream upon contact with such materials of this invention, and to produce a treated feed stream having a reduced amount of impurities. Such feed streams are used as feed to hydrocarbon conversion processes, for example, aromatic alkylation or transalkylation processes. The untreated stream having such impurities comprises one or more alkylatable aromatic compound streams. In one or more embodiments, the untreated stream further comprises as an option one or more alkylating agent streams. The impurities in such untreated stream comprise compounds having at least one of the following elements: nitrogen, halogens, oxygen, sulfur, arsenic, selenium, tellurium, phosphorus, and Group 1 through Group 12 metals.

This method may be practiced inside a vessel (i.e., in-situ), for example in a guard bed vessel, or outside of a vessel (i.e., ex-situ).

Use of the Materials in Processes for Producing Mono-Alkylated Aromatic Compounds The material of this invention, preferably a guard bed material, may be used in processes for producing mono-alkylated aromatic compounds. In one or more embodiments, the process comprises the step of contacting a treated feed stream and an alkylating agent stream with an alkylation or transalkylation catalyst composition under alkylation or transalkylation conditions to produce an effluent stream comprising said mono-alkylated aromatic compound stream. In one or more embodiments, the treated feed stream is made by the method for removing catalyst poisons of this invention, described above.

In other embodiments, the process for producing a mono-alkylated aromatic compound stream comprises a step for making the guard bed material in which a material is contacted with a humid gas and/or water, and then drying said material with a drying gas at a temperature as disclosed herein, preferably at a temperature greater than about 200° C., to produce a guard bed material having an increased collidine uptake at 200° C. The humid gas has a relative humidity as disclosed herein, preferably in the range of greater than or equal to about 50% to less than or equal to about 100%. The water is at a temperature as disclosed herein, preferably at a temperature in the range of greater than or equal to about 0° C. to less than or equal to about 100° C. In one or more embodiments, this step further comprising a guard bed vessel which contains said material, wherein said drying of the material is conducted in-situ in said guard bed vessel.

In the next step, the guard bed material is contacted with an untreated stream having one or more impurities to remove at least a portion of said impurities and to produce a treated feed stream having a reduced amount of impurities. The impurities are adsorbed by the material. In one or more embodiments, the untreated stream comprising one or more alkylatable aromatic compound streams, optionally one or more alkylating agent streams.

In one or more embodiments, the untreated stream comprising one or more alkylatable aromatic compound streams, optionally one or more alkylating agent streams is contacted with a guard bed material of this invention at a temperature in the range of from greater than or equal to 25° C., or 50° C., or 75° C., or 100° C., or 150° C., or 175° C. up to less than or equal to 200° C.

This step may be practiced inside a vessel (i.e., in-situ), for example in a guard bed vessel that is in fluid communication with an alkylation or transalkylation vessel. Optionally, the step may be practiced outside of a vessel (i.e., ex-situ), in an open-air vessel.

In the next step, the treated feed stream and an alkylating agent stream are contacted with an alkylation or transalkylation catalyst composition under alkylation or transalkylation conditions to produce an effluent stream comprising said mono-alkylated aromatic compound stream. The alkylation or transalkylation catalyst has a longer cycle length due to the removal of the catalyst poisons by the guard bed catalyst. This step may be practiced inside an alkylation and/or transalkylation vessel that is in fluid communication with the guard bed vessel, referenced above, such that the contacting with the guard bed material is practiced in-situ.

In another step of this process, said treated feed stream and an alkylating agent stream are contacted with an alkylation or transalkylation catalyst composition under alkylation or transalkylation conditions to produce an effluent stream comprising said mono-alkylated aromatic compound stream.

In operation of one or more embodiments of this invention, the guard bed material is used to remove impurities (as defined herein) from the untreated feed streams that are supplied to a process for hydrocarbon conversion, such as, for example, a process for producing mono-alkylated aromatic compounds stream. The untreated stream having one or more impurities is contacted with the guard bed material of this invention, which is contained or disposed within, in one or more embodiments, in a guard bed vessel, to remove at least a portion of the impurities and to produce a treated feed stream having a reduced amount of impurities. In one or more embodiments, the untreated stream comprises one or more alkylatable aromatic compound streams, optionally one or more alkylating agent streams. The treated feed stream having a reduced amount of impurities and an alkylating agent stream are then contacted with an alkylation catalyst composition under alkylation conditions, or a transalkylation catalyst composition under transalkylation conditions, to produce an effluent stream comprising the mono-alkylated aromatic compound stream. As a result of the use of the treated guard bed material, the cycle length of the alkylation or transalkylation catalyst composition used, for example, in aromatic alkylation processes is increased.

Not to bound by any theory, it is believed that the treated guard bed material of this invention has an increased capacity to adsorb catalyst poisons, as measured by collidine uptake at 200° C., because there is a significant increase in the number of pores on the surface of the material that are available for adsorption of impurities or an increase in the number of acid sites for adsorption of impurities, including, but not limited to, organic nitrogenous impurities. When the untreated guard bed material is dried with a drying gas, preferably, at a temperature of greater than 200° C., any impurities or other matter that is adsorbed onto the pores on the surface of the guard bed material are thereby desorbed. Optionally, the guard bed material is contacted with water or humid gas prior to being dried to produce a humidified guard bed material. When the humidified guard bed material is dried with a drying gas, preferably, at a temperature of greater than about 200° C., the water is removed along with other impurities or other matters are desorbed making available a greater number of pores on the surface of the material that are available for absorption of impurities.

Reaction products which may be obtained from the process for producing a mono-alkylated aromatic compound stream of the invention include ethylbenzene from the reaction of benzene with ethylene, cumene from the reaction of benzene with propylene, ethyltoluene from the reaction of toluene with ethylene, cymenes from the reaction of toluene with propylene, and sec-butylbenzene from the reaction of benzene and n-butenes.

The alkylation process of the invention is particularly intended to produce mono-alkylated aromatic compounds, such as, for example, ethylbenzene and cumene, but the alkylation step will normally produce some poly-alkylated aromatic compounds. Thus, the process includes the further steps of separating a poly-alkylated aromatic compound stream from the alkylation effluent stream comprising the mono-alkylated aromatic compound stream, and then contacting the poly-alkylated aromatic compound stream and additional alkylatable aromatic compound stream with a transalkylation catalyst under suitable transalkylation conditions to produce an additional mono-alkylated aromatic compound stream.

Alkylation Catalyst and/or Transalkylation Catalyst

In one or more embodiments, the alkylation catalyst and/or the transalkylation catalyst comprises a molecular sieve selected from the group consisting of beta, faujasite, mordenite, and a MCM-22 family molecular sieve (as defined herein), and mixtures thereof, which have been found to be useful in alkylation processes for production of mono-alkylated aromatic compounds.

In one or more embodiments, the faujasite molecular sieve is selected from the group consisting of 13X, low sodium ultrastable Y (USY), dealuminized Y (Deal Y), ultrahydrophobic Y (UHP-Y), rare earth exchanged Y (REY), rare earth exchanged USY (RE-USY), and mixtures thereof. In one or more embodiments, the mordenite molecular sieve is selected from the group consisting of mordenite, TEA-mordenite and mixtures thereof. In one or more embodiments, the MCM-22 family molecular sieve is selected from the group consisting of MCM-22, MCM-36, MCM-49, MCM-56, EMM-10, EMM-10-P, EMM-12, EMM-13, UZM-8, UZM-8HS, ITQ-1, ITQ-2, ITQ-30 and mixtures thereof.

In other embodiments, the alkylation catalyst and/or the transalkylation catalyst comprises a molecular sieve having a framework type selected from the group consisting of FAU (e.g., faujasite), MOR (e.g., mordenite), *BEA (e.g., zeolite beta), and mixtures thereof.

The molecular sieve can be combined in conventional manner with an oxide binder, such as alumina or silica, such that the final alkylation catalyst and/or transalkylation contains between 1 and 100 wt. % of the molecular sieve.

In one or more embodiments, said alkylation or transalkylation catalyst can be a fresh alkylation or transalkylation catalyst, an at least partially deactivated alkylation or transalkylation catalyst, or combinations thereof. In one or more embodiments, said at least partially deactivated alkylation or transalkylation catalyst was deactivated by coke deposition during its prior use in an alkylation or transalkylation process.

Alkylatable Aromatic Compounds

Substituted alkylatable aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable alkylatable aromatic hydrocarbons for any one of the embodiments of this invention include benzene, naphthalene, anthracene, naphthacene, perylene, coronene, and phenanthrene, with benzene being preferred.

Generally the alkyl groups, which can be present as substituents on the aromatic compound, contain from 1 to about 22 carbon atoms and usually from about 1 to 8 carbon atoms, and most usually from about 1 to 4 carbon atoms.

Suitable alkyl substituted aromatic compounds for any one of the embodiments of this invention include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalene; ethylnaphthalene; 2,3-dimethylanthracene; 9-ethylanthracene; 2-methylanthracene; o-methylanthracene; 9,10-dimethyl phenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecyltoluene, etc.

Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes made in such instances may be less than about 500 ppm.

Reformate containing substantial quantities of benzene, toluene and/or xylene constitutes a useful feed for the process of this invention.

Alkylating Agents

The alkylating agents, which are useful in one or more embodiments of this invention, generally include any aliphatic or aromatic organic compound having one or more available alkylating olefinic groups capable of reaction with the alkylatable aromatic compound, preferably with the alkylating group possessing from 1 to 5 carbon atoms, or poly-alkylated aromatics compound(s). Examples of suitable alkylating agents for any one of the embodiments of this invention are olefins such as ethylene, propylene, the butenes, and the pentenes; alcohols (inclusive of monoalcohols, dialcohols, trialcohols, etc.), such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth.

Mixtures of light olefins are especially useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein.

Poly-alkylated aromatic compounds suitable for one or more embodiments of this invention include, but are not limited to, polyethylbenzene(s), polyisporpoylebenzene(s) or mixtures thereof.

For example, a typical FCC light olefin stream possesses the following composition as shown in Table I:

TABLE I

|  | Wt. % | Mol. % |
| --- | --- | --- |
| Ethane | 3.3 | 5.1 |
| Ethylene | 0.7 | 1.2 |

TABLE I-continued

|  | Wt. % | Mol. % |
| --- | --- | --- |
| Propane | 14.5 | 15.3 |
| Propylene | 42.5 | 46.8 |
| Isobutane | 12.9 | 10.3 |
| n-butane | 3.3 | 2.6 |
| Butenes | 22.1 | 18.32 |
| Pentanes | 0.7 | 0.4 |

Alkylation and/or Transalkylation Conditions

In one or more embodiments, the alkylation and/or transalkylation processes of this invention is conducted such that the organic reactants, i.e., the alkylatable aromatic compound and the alkylating agent, are brought into contact with an alkylation or transalkylation catalyst in a suitable alkylation or transalkylation reaction zone such as, for example, in a flow reactor containing a fixed bed of the catalyst composition, under effective and suitable alkylation and/or transalkylation conditions.

Such alkylation conditions can include at least one of the following: a temperature of from about 10° C. and about 400° C., or from about 10° C. to about 200° C., or from about 150° C. to about 300° C., a pressure up to about 25000 kPa, or up to about 20000 kPa, or from about 100 kPa to about 7000 kPa, or from about 689 kPa to about 4601 kPa, a molar ratio of alkylatable aromatic compound to alkylating agent of from about 0.1:1 to about 50:1, preferably from about 0.5:1 to 10:1, and a feed weight hourly space velocity (WHSV) of between about 0.1 and about 100 hr$^{-1}$, or from about 0.5 to 50 hr$^{-1}$, or from about 10 hr$^{-1}$ to about 100 hr$^{-1}$.

The reactants can be in either the vapor phase or in the liquid phase, or in the at least partially liquid phase. In one or more embodiments, the reactants can be neat, i.e., free from intentional admixture or dilution with other material, or they can include carrier gases or diluents such as, for example, hydrogen or nitrogen.

When benzene is alkylated with ethylene to produce ethylbenzene, the alkylation reaction may be carried out under at least partially liquid phase conditions including a temperature between about 150° C. and 300° C., or between about 200° C. and 260° C., a pressure up to about 20000 kPa, preferably from about 200 kPa to about 5600 kPa, a WHSV of from about 0.1 hr$^{-1}$ to about 50 hr$^{-1}$, or from about 1 hr$^{-1}$ and about 10 hr$^{-1}$ based on the ethylene feed, and a ratio of the benzene to the ethylene in the alkylation reactor from 1:1 to 30:1 molar, preferably from about 1:1 to 10:1 molar.

When benzene is alkylated with propylene to produce cumene, the reaction may be carried out under at least partially liquid phase conditions including a temperature of up to about 250° C., preferably from about 10° C. to about 200° C.; a pressure up to about 25000 kPa, preferably from about 100 kPa to about 3000 kPa; and a WHSV of from about 1 hr$^{-1}$ to about 250 hr$^{-1}$, preferably from 5 hr$^{-1}$ to 50 hr$^{-1}$, preferably from about 5 hr$^{-1}$ to about 10 hr$^{-1}$ based on the ethylene feed.

Such transalkylation conditions can include at least one of the following: a temperature of about 100° C. to about 300° C., or from about 100° C. to about 275° C., a pressure of about 200 kPa to about 600 kPa, or about 200 kPa to about 500 kPa, a weight hourly space velocity (WHSV) based on the total feed of about 0.5 hr$^{-1}$ to about 100 hr$^{-1}$ on total feed, and aromatic/poly-alkylated aromatic compound weight ratio 1:1 to 6:1.

When the poly-alkylated aromatic compounds are poly-ethylbenzenes and are reacted with benzene to produce ethylbenzene, the transalkylation conditions include a temperature of from about 220° C. to about 260° C., a pressure of from about 300 kPa to about 400 kPa, weight hourly space velocity of 2 to 6 on total feed and benzene/PEB weight ratio 2:1 to 6:1.

When the poly-alkylated aromatic compounds are poly-isopropylbenzenes (PIPBs) and are reacted with benzene to produce cumene, the transalkylation conditions include a temperature of from about 100° C. to about 200° C., a pressure of from about 300 kPa to about 400 kPa, a weight hourly space velocity of 1 to 10 on total feed and benzene/PIPB weight ratio 1:1 to 6:1.

The invention is described in the following numbered paragraphs.

Paragraph 1. A method of making a material having an increased capacity to adsorb catalyst poisons, said method comprising the steps of contacting said material with humid gas, and then drying said material with a drying gas at a temperature greater than or equal to about 200° C. to produce said material having an increased collidine uptake at 200° C., wherein said material comprising a molecular sieve and said humid gas has a relative humidity in the range of greater than or equal to about 50% to less than or equal to about 100%.

Paragraph 2. The method of Paragraph 1, wherein said humid gas is selected from the group consisting of air, oxygen, nitrogen and mixtures thereof.

Paragraph 3. A method of making a material having an increased capacity to adsorb catalyst poisons, said method comprising the steps of contacting said material with water, and then drying said material with a drying gas at a temperature greater than about 200° C. to produce said material having an increased collidine uptake at 200° C. to less than or equal to about 550° C., wherein said material comprising a molecular sieve and said water has a temperature in the range of greater than or equal to about 0° C. to less than or equal to about 100° C.

Paragraph 4. The method of any one of Paragraphs 1 to 3, wherein said drying gas is selected from the group consisting of air, oxygen, nitrogen and mixtures thereof.

Paragraph 5. The method of any one of Paragraphs 1 to 4, wherein said drying step is conducted in-situ inside of a vessel.

Paragraph 6. A guard bed material made by the method of any one of Paragraphs 1 to 5.

Paragraph 7. A method for removing catalyst poisons from untreated feed stream having one or more impurities, the method comprising the step of contacting an untreated stream with a material made by the method of any one of claims 1 to 5 or a guard bed material of Paragraph 6, to remove at least a portion of said impurities and to produce a treated feed stream having a reduced amount of impurities, wherein said untreated stream comprising one or more alkylatable aromatic compound streams, optionally one or more alkylating agent streams, wherein said impurities comprising compounds having at least one of the following elements: nitrogen, halogens, oxygen, sulfur, arsenic, selenium, tellurium, phosphorus, and Group 1 through Group 12 metals.

Paragraph 8. A process for producing a mono-alkylated aromatic compound stream comprising the step of contacting a treated feed stream of Paragraph 7 and an alkylating agent stream with an alkylation or transalkylation catalyst composition under alkylation or transalkylation conditions to produce an effluent stream comprising said mono-alkylated aromatic compound stream.

Paragraph 9. A process for producing a mono-alkylated aromatic compound stream comprising the steps of:

(a) contacting a material with a humid gas, and then drying said material with a drying gas at a temperature greater than about 200° C. to produce a guard bed material having an increased collidine uptake at 200° C., wherein said humid gas has a relative humidity in the range of greater than or equal to about 50% to less than or equal to about 100%;
(b) contacting an untreated stream having one or more impurities with said guard bed material of step (a) to remove at least a portion of said impurities and to produce a treated feed stream having a reduced amount of impurities, wherein said untreated stream comprising one or more alkylatable aromatic compound streams, optionally one or more alkylating agent streams; and
(c) contacting said treated feed stream of step (b) and an alkylating agent stream with an alkylation or transalkylation catalyst composition under alkylation or transalkylation conditions to produce an effluent stream comprising said mono-alkylated aromatic compound stream.

Paragraph 10. The process of Paragraph 9, further comprising a guard bed vessel which comprises said material, and wherein said contacting step (a) is conducted in-situ in said guard bed vessel.

Paragraph 11. The process of Paragraphs 9 or 10, wherein said untreated stream is contacted with said guard bed material of step (a) at a temperature in the range of from 25° C. to 200° C.

Paragraph 12. The process of Paragraphs 9 to 11, wherein said impurities comprising compounds having at least one of the following elements: nitrogen, halogens, oxygen, sulfur, arsenic, selenium, tellurium, phosphorus, and Group 1 through Group 12 metals.

Paragraph 13. The process of any one of Paragraphs 9 to 11, wherein said humid gas is selected from the group consisting of air, oxygen, nitrogen and mixtures thereof.

Paragraph 14. The process of any one of Paragraphs 9 to 13, wherein said drying gas is selected from the group consisting of air, oxygen, nitrogen and mixtures thereof.

Paragraph 15. The process of any one of Paragraphs 9 to 14, wherein said material is dried at a temperature in the range of greater than or equal to about 200° C. to less than or equal to about 550° C.

Paragraph 16. The process of any one of Paragraphs 8 to 15, wherein said alkylation or transalkylation catalyst composition comprising a molecular sieve selected from the group consisting of beta, faujasite, mordenite, and a MCM-22 family molecular sieve and mixtures thereof.

Paragraph 17. The process of Paragraph 16, wherein said faujasite molecular sieve is selected from the group consisting of 13X, low sodium ultrastable Y (USY), dealuminized Y (Deal Y), ultrahydrophobic Y (UHP-Y), rare earth exchanged Y (REY), rare earth exchanged USY (RE-USY), and mixtures thereof.

Paragraph 18. The process of Paragraph 16, wherein said mordenite molecular sieve is selected from the group consisting of mordenite, TEA-mordenite and mixtures thereof.

Paragraph 19. The process of Paragraph 16, wherein said MCM-22 family molecular sieve is selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30 and mixtures thereof.

Paragraph 20. The process of any one of Paragraphs 8 to 19, wherein said alkylating agent stream comprising an olefinic compound having 1 to 5 carbon atoms or a poly-alkylated aromatic compound.

Paragraph 21. The process of any one of Paragraphs 8 to 19, wherein said alkylating agent stream comprising ethylene, propylene or mixtures thereof.

Paragraph 22. The process of any one of Paragraphs 8 to 19, wherein said alkylating agent stream comprising polyethylbenzene(s), polyisopropylbenzene(s) or mixtures thereof.

Paragraph 23. The process of any one of Paragraphs 8 to 22, wherein said alkylatable aromatic compound stream comprising benzene.

Paragraph 24. The process of any one of Paragraphs 8 to 23, wherein said alkylation conditions are at least partially liquid phase conditions and include a temperature of 10° C. to 400° C. and a pressure of up to about 25000 kPa, and a WHSV based on the weight of said alkylating agent from about 0.1 hr-1 to about 100 hr-1.

Paragraph 25. The process of any one of Paragraphs 8 to 24, wherein said transalkylation conditions are at least partially liquid phase conditions, and include a temperature of from about 100° C. to about 300° C., a pressure of about 200 kPa to about 600 kPa, and a WHSV based on the weight of said alkylating agent from about 0.5 hr-1 to about 100 hr-1.

EXAMPLES

The invention will now be more particularly described with reference to the following Examples.

Loss-On-Ignition (LOI) and Collidine Uptake Procedures

The Loss-on-Ignition (LOI) at 525° C. was measured using a solids analyzer (Model No. 601 TGA, LECO Corporation) as follows: A known amount of a sample to be measured is heated in oxygen to a prescribed temperature (525° C.) while the weight of the sample is monitored during the operation. When the sample reaches the requested temperature, the weight change, if any, is monitored until there is no recordable change, as defined by the operator or method.

Collidine uptake was determined using a collidine adsorption test. In the collidine adsorption test, samples were analyzed using a TA Instruments (Model TA2950) Thermal Gravimetric Analyzer with a modified gas/vapor delivery system. Sample size usually ranged from 25 to 75 mg. The sample was first dried for 60 minutes in nitrogen flowing at 90 cc/min. at 200° C. or 500° C., based on the drying condition in the respective Example. The drying step may be extended if a stable weight is not achieved within the 60 minutes. The collidine was then delivered to the sample for a period of 60 minutes. This was accomplished by bubbling nitrogen through a sparger containing collidine at a rate of 90 cc/min. The sparger was maintained at a temperature of 35° C. En route to the sample, the collidine vapor passed through a glass condenser 8" in length that was maintained at a temperature of 26° C., which fixed the collidine vapor pressure. The path downstream of the condenser to the sample was heat traced to prevent any condensation before reaching the sample. The sample is maintained at 200° C. during the adsorption. The adsorption step was followed by a stripping step where the sample was subjected to 90 cc/min of dry nitrogen while holding sample at a temperature of 200° C. The stripping was done for 60 minutes. The amount of collidine adsorbed was determined by difference in weight between the weight at the end of the drying step and the final weight (after the stripping step). Collidine uptake was reported in millimoles/gram of sample (mmol/g).

Example 1

The material was comprised of 80 wt. % USY zeolite (in hydrogen form and having a $SiO_2/Al_2O_3$ molar ratio of 60, 0.03 wt. % $Na_2O$, surface area of 720 $m^2/g$ and commercially available from Zeolyst International) and 20 wt. % $Al_2O_3$. The Loss-on-Ignition (LOI) at 525° C. was measured, and the collidine uptake was measured at 200° C., as described above.

Example 2

The material of Example 1 was pre-humidified with saturated flowing air at ambient temperature of 20-25° C. for 24 hours. The Loss-on-Ignition (LOI) at 525° C. was measured, and the collidine uptake was measured at 200° C. after pre-drying at 200° C. and 500° C., as described above.

Example 3

The material was comprised of 80 wt. % USY zeolite (in hydrogen form having a $SiO_2/Al_2O_3$ molar ratio of 30, 0.03 wt. % $Na_2O$, and a surface area of 780 $m^2/g$) and 20 wt. % $Al_2O_3$. The Loss-on-Ignition (LOI) at 525° C. was measured, and the collidine uptake was measured at 200° C., as described above.

Example 4

The material of Example 3 was pre-humidified with saturated flowing air at ambient temperature of 20-25° C. for 24 hours. The Loss-on-Ignition (LOI) at 525° C. was measured, and the collidine uptake was measured at 200° C. after pre-drying at 200° C. and 500° C., as described above.

Example 5

The material was comprised of 100 wt. % 13X molecular sieve (in sodium form and having a $SiO_2/Al_2O_3$ molar ratio of 2.8±0.2). The Loss-on-Ignition (LOI) at 525° C. was measured, and the collidine uptake was measured at 200° C. after pre-drying at 200° C. and 500° C., as described above.

Example 6

The material of Example 5 was pre-humidified with saturated flowing air at ambient temperature of 20-25° C. for 24 hours. The Loss-on-Ignition (LOI) at 525° C. was measured, and the collidine uptake was measured at 200° C. after pre-drying at 200° C. and 500° C. after pre-drying at 200° C. and 500° C., as described above.

Example 7

The material was comprised of 80 wt. % zeolite beta (made according U.S. Pat. No. 3,308,069) and 20 wt. % $Al_2O_3$. The Loss-on-Ignition (LOI) at 525° C. was measured, and the collidine uptake was measured at 200° C. after pre-drying at 200° C. and 500° C. after pre-drying at 200° C. and 500° C., as described above.

Example 8

The material of Example 7 was pre-humidified with saturated flowing air at ambient temperature of 20-25° C. for 24 hours. The Loss-on-Ignition (LOI) at 525° C. was measured, and the collidine uptake at 200° C. was measured after pre-drying at 200° C. and 500° C., as described above.

The experimental parameters and properties of the materials of Examples 1 to 8 are shown in Table II, below. As can be seen, the collidine uptake at 200° C. increased after pre-drying as the drying temperature was increased from 200° C. to 500° C.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

TABLE II

| Example | Description | Pre-Humidified | Type of Humidification | After Humidification | Water Content, wt. % LOI @ 525° C. | Drying Temp ° C. Collidine Uptake @ 200° C., mmol/g After Pre-Drying @ 200° C. | After Pre-Drying @ 500° C. |
|---|---|---|---|---|---|---|---|
| 1 | 80% USY, 20% $Al_2O_3$ | No | None | None | 2.6 | 253, 264 | 332 |
| 2 | 80% USY, 20% $Al_2O_3$ | Yes | Humid Air | None | 9.6 | 261 | 332 |
| 3 | 80% USY, 20% $Al_2O_3$ | No | None | None | 2.4 | 354, 342 | 439 |
| 4 | 80% USY, 20% $Al_2O_3$ | Yes | Humid Air | None | 21 | 406 | 461 |
| 5 | Sigma Aldrich 13X | No | None | None | n.a. | 482 | 706 |
| 6 | Sigma Aldrich 13X | Yes | Humid Air | None | 2.8 | 467 | 773 |
| 7 | 80% Beta, 20% $Al_2O_3$ | No | None | None | 2.8 | 557 | 638 |
| 8 | 80% Beta, 20% $Al_2O_3$ | Yes | Humid Air | None | 17.9 | 290 | 638 |

What is claimed is:

1. A process for producing a mono-alkylated aromatic compound stream comprising the steps of:
   (a) providing a material comprising a molecular sieve, said material having a first collidine uptake at 200° C.;
   (b) drying said material in a shallow moving bed dryer having a material deposit height of less than about 1 meter with a drying gas at a temperature greater than about 200° C. to produce a guard bed material having a second collidine uptake at 200° C., wherein said second collidine uptake is greater than said first collidine uptake;
   (c) contacting an untreated stream having one or more impurities with said guard bed material of step (b) to remove at least a portion of said impurities and to produce a treated feed stream having a reduced amount of impurities, wherein said untreated stream comprising one or more alkylatable aromatic compound streams, optionally one or more alkylating agent streams; and
   (d) contacting said treated feed stream of step (c) and an alkylating agent stream with an alkylation catalyst composition under alkylation condition or a transalkylation catalyst composition under transalkylation conditions to produce an effluent stream comprising said mono-alkylated aromatic compound stream.

2. The process of claim 1, wherein said material is disposed in a guard bed vessel, and wherein said contacting step (c) is conducted in-situ inside said guard bed vessel.

3. The process of claim 1, wherein said dryer is a fixed bed dryer, and said drying gas flows through said material.

4. The process of claim 1, wherein said drying gas is selected from the group consisting of air, oxygen, nitrogen and mixtures thereof.

5. The process of claim 1, wherein said material is dried at a temperature in the range of greater than or equal to about 200° C. to less than or equal to about 550° C.

6. The process of claim 1, wherein said drying is conducted for a period of about 1 hour to 36 hours.

7. The process of claim 1, wherein said impurities comprising compounds having at least one of the following elements: nitrogen, halogens, oxygen, sulfur, arsenic, selenium, tellurium, phosphorus, and Group 1 through Group 12 metals.

8. The process of claim 1, wherein said alkylation catalyst composition or said transalkylation catalyst composition comprising a molecular sieve selected from the group consisting of beta, faujasite, mordenite, and a MCM-22 family molecular sieve and mixtures thereof, wherein said MCM-22 family materials are characterized by having an X-ray diffraction pattern including d-spacing maxima at 12.4±0.25, 3.57±0.07 and 3.42±0.07 Angstroms (either calcined or as-synthesized).

9. The process of claim 8, wherein said faujasite molecular sieve is selected from the group consisting of 13X, low sodium ultrastable Y (USY), dealuminized Y (Deal Y), ultrahydrophobic Y (UHP-Y), rare earth exchanged Y (REY), rare earth exchanged USY (RE-USY), and mixtures thereof.

10. The process of claim 8, wherein said mordenite molecular sieve is selected from the group consisting of mordenite, TEA-mordenite and mixtures thereof.

11. The process of claim 8, wherein said MCM-22 family molecular sieve is selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30 and mixtures thereof.

12. The process of claim 1, wherein said alkylating agent stream comprising an olefinic compound having 1 to 5 carbon atoms or a poly-alkylated aromatic compound.

13. The process of claim 1, wherein said alkylating agent stream comprising ethylene, propylene or mixtures thereof.

14. The process of claim 1, wherein said alkylating agent stream comprising polyethylbenzene(s), polyisopropylbenzene(s) or mixtures thereof.

15. The process of claim 1, wherein said alkylatable aromatic compound stream comprising benzene.

16. The process of claim 1, wherein said alkylation conditions are at least partially liquid phase conditions and include a temperature of 10° C. to 400° C. and a pressure of up to about 25000 kPa, and a WHSV based on the weight of said alkylating agent from about 0.1 $hr^{-1}$ to about 100 $hr^{-1}$.

17. The process of claim 1, wherein said transalkylation conditions are at least partially liquid phase conditions, and include a temperature of from about 100° C. to about 300° C., a pressure of about 200 kPa to about 600 kPa, and a WHSV based on the weight of said alkylating agent from about 0.5 $hr^{-1}$ to about 100 $hr^{-1}$.

* * * * *